(12) United States Patent
Kono et al.

(10) Patent No.: US 11,331,426 B2
(45) Date of Patent: May 17, 2022

(54) INFUSION PUMP

(71) Applicants: ICOMES LAB Co., Ltd., Iwate (JP);
NIPRO CORPORATION, Osaka (JP)

(72) Inventors: Katsuya Kono, Iwate (JP); Ryoichi Akai, Osaka (JP); Shinji Akitomi, Saitama (JP)

(73) Assignees: ICOMES LAB Co., Ltd., Iwate (JP);
NITRO CORPORATION, Osaka (JP)

( * ) Notice: Subject to any disclaimer, the term of this patent is extended or adjusted under 35 U.S.C. 154(b) by 141 days.

(21) Appl. No.: 16/496,358

(22) PCT Filed: Mar. 22, 2018

(86) PCT No.: PCT/JP2018/011478
§ 371 (c)(1),
(2) Date: Nov. 18, 2019

(87) PCT Pub. No.: WO2018/174181
PCT Pub. Date: Sep. 27, 2018

(65) Prior Publication Data
US 2020/0139044 A1  May 7, 2020

(30) Foreign Application Priority Data

Mar. 22, 2017 (JP) .............................. JP2017-056410

(51) Int. Cl.
*A61M 5/152* (2006.01)
*A61M 5/142* (2006.01)
*A61M 5/145* (2006.01)

(52) U.S. Cl.
CPC ........ *A61M 5/152* (2013.01); *A61M 5/14232* (2013.01); *A61M 2005/14506* (2013.01);
(Continued)

(58) Field of Classification Search
CPC .............. F04B 43/1276; F04B 43/1253; F04B 43/1261; F04B 43/1284; A61M 60/279;
(Continued)

(56) References Cited

U.S. PATENT DOCUMENTS 2,831,437 A * 4/1958 Cromwell ............... F04B 43/12
417/477.5
3,918,854 A * 11/1975 Catarious ............ F04B 43/1284
417/477.11
(Continued)

FOREIGN PATENT DOCUMENTS

CN 87200265 U 11/1987
CN 2688299 Y 3/2005
(Continued)

OTHER PUBLICATIONS

International Search Report issued in corresponding PCT/JP2018/011478, dated May 15, 2018, with English translation.
(Continued)

*Primary Examiner* — Emily L Schmidt
*Assistant Examiner* — Joshua Parker Reddington
(74) *Attorney, Agent, or Firm* — McDermott Will & Emery LLP (57) ABSTRACT

An infusion pump includes: infusion-tube pressing parts configured to press a flexible infusion tube; an infusion-tube receiving surface configured to serve as a receiving surface when the infusion-tube pressing parts press the infusion tube; and a restoration device provided between the infusion-tube pressing parts, the restoration device being configured to move together with the infusion-tube pressing parts along the infusion-tube receiving surface and to press two sides of the infusion tube pressed by the infusion-tube pressing parts, wherein the infusion-tube pressing parts is configured to move sequentially in a longitudinal direction
(Continued)

of the infusion tube along the infusion-tube receiving surface to deliver a liquid in the infusion tube in one direction while pressing the infusion tube by sandwiching the infusion tube with the infusion-tube receiving surface.

7 Claims, 11 Drawing Sheets

(52) U.S. Cl.
CPC ............... *A61M 2205/103* (2013.01); *A61M 2205/3365* (2013.01); *A61M 2205/505* (2013.01)

(58) Field of Classification Search
CPC ............. A61M 5/14232; A61M 5/152; A61M 2005/14506; A61M 2205/103; A61M 2205/3365
See application file for complete search history.

(56) References Cited

U.S. PATENT DOCUMENTS

| | | | | |
|---|---|---|---|---|
| 5,340,290 A | * | 8/1994 | Clemens | A61M 5/14232 417/477.1 |
| 6,468,242 B1 | * | 10/2002 | Wilson | A61M 5/172 604/65 |
| 8,529,229 B2 | * | 9/2013 | Asai | B41J 2/16532 417/477.8 |
| 2006/0002799 A1 | * | 1/2006 | Schann | F04B 49/065 417/1 |
| 2014/0212314 A1 | | 7/2014 | Baron | |
| 2018/0058438 A1 | * | 3/2018 | Ochoa | A61M 1/75 |

FOREIGN PATENT DOCUMENTS

| | | |
|---|---|---|
| EP | 1 978 256 A1 | 10/2008 |
| EP | 2 902 047 A1 | 8/2015 |
| EP | 3323447 A1 | 5/2018 |
| JP | H9-310684 A | 12/1997 |
| JP | 2006-17123 A | 1/2006 |
| JP | 2014-521886 A | 8/2014 |
| JP | 2016-128014 A | 7/2016 |

OTHER PUBLICATIONS

Extended European Search Report issued in corresponding European Patent Application No. 18770914.2-1122, dated Jul. 30, 2020.
Chinese Office Action issued in corresponding Chinese Patent Application No. 201880033038.5, dated Apr. 2, 2021, with English translation.

* cited by examiner

INFUSION PUMP

CROSS-REFERENCE OF RELATED APPLICATIONS

This application is the U.S. National Phase under 35 U.S.C. § 371 of International Patent Application No. PCT/JP2018/011478, filed on Mar. 22, 2018, which in turn claims the benefit of Japanese Application No. 2017-056410, filed Mar. 22, 2017, the entire disclosures of which Applications are incorporated by reference herein.

FIELD

The present invention relates to an infusion pump.

BACKGROUND

There is a conventional infusion pump for administering a chemical solution into a body (see Patent Literature 1). The infusion pump includes a rotor unit including a plurality of rollers and, by rotating the rotor unit, sequentially presses a flexible infusion tube with the roller to deliver a solution.

CITATION LIST

Patent Literature

Patent Literature 1: Japanese Laid-open Patent Publication No. 2016-128014

SUMMARY

Technical Problem

An infusion tube applied to this type of infusion pump needs to be elastic so as to be restored into the original form after it is pressed by the roller. For this reason, conventionally, a silicon infusion tube or a vinyl chloride infusion tube is applied. Unfortunately, silicon infusion tubes are not desirable from the aspect of cost as they need to be manufactured for a specific use.

On the other hand, vinyl chloride infusion tubes are not always desirable in terms of restorability even though they are widely used for drip infusion and therefore inexpensive. Therefore, as described above, when the vinyl chloride infusion tubes repeatedly receives a pressing force from the roller, it remains crushed, which may cause a problem such as a significant change in the flow rate.

The present invention has been made in consideration of the foregoing, and it has an object to provide an infusion pump that is suitable for use even with a vinyl chloride infusion tube that is widely used at low cost.

Solution to Problem

To solve the problem and achieve the object, an infusion pump according to the present invention includes: infusion-tube pressing parts configured to press a flexible infusion tube; and an infusion-tube receiving surface configured to serve as a receiving surface when the infusion-tube pressing parts press the infusion tube, the infusion-tube pressing parts being configured to move sequentially in a longitudinal direction of the infusion tube along the infusion-tube receiving surface to deliver a liquid in the infusion tube in one direction while pressing the infusion tube by sandwiching the infusion tube with the infusion-tube pressing parts and the infusion-tube receiving surface, wherein a restoration mechanism configured to move together with the infusion-tube pressing parts along the infusion-tube receiving surface and to press two sides of the infusion tube pressed by the infusion-tube pressing parts is provided between the infusion-tube pressing parts.

Moreover, in the infusion pump according to the present invention, the restoration mechanism includes an infusion-tube insertion part having a space for passing the infusion tube, the infusion-tube insertion part including: a first insertion part; and a second insertion part having a smaller space for passing the infusion tube as compared with the first insertion part, wherein the first insertion part and the second insertion part are disposed such that the second insertion part passes the infusion tube after the first insertion part passes the infusion tube.

Moreover, the infusion pump according to the present invention further includes a pair of infusion-tube holding parts configured to hold the infusion tube in a longitudinal direction of the infusion-tube receiving surface at areas on two sides with the infusion-tube receiving surface interposed therebetween.

Moreover, in the infusion pump according to the present invention, the infusion-tube pressing parts and the infusion-tube receiving surface are movable to have a wider space between each other, and when the infusion-tube pressing parts and the infusion-tube receiving surface moves from a state of having a wide space between each other to a state where the infusion tube is pressed by the infusion-tube pressing parts and the infusion-tube receiving surface, the pair of infusion-tube holding parts are moved in a direction away from each other, while holding the infusion tube, before the infusion tube is pressed by the infusion-tube pressing parts and the infusion-tube receiving surface.

Moreover, in the infusion pump according to the present invention, a part of the infusion-tube receiving surface abutting the infusion tube is provided with a recess and a protrusion to prevent a relative movement of the infusion tube.

Moreover, the infusion pump according to the present invention further includes: a rotor unit that is disposed to be rotatable around a rotary shaft, the rotor unit being configured to support the infusion-tube pressing parts on a circumference around the rotary shaft and to support the restoration mechanism between the infusion-tube pressing parts; and an infusion-tube receiving member that is formed such that, when the infusion tube is pressed by the infusion-tube pressing parts and the infusion-tube receiving surface, the infusion-tube receiving surface has a circular shape with the rotary shaft of the rotor unit as a center.

Moreover, the infusion pump according to the present invention further includes: a motor configured to rotate the rotor unit; and a planetary-gear reduction mechanism provided between the motor and the rotor unit such that a rotary shaft of a sun gear is parallel to the rotary shaft of the rotor unit.

Moreover, the infusion pump according to the present invention further includes: a motor configured to rotate the rotor unit; and a control unit configured to control a rotating velocity of the motor, wherein when the rotor unit is rotated and the infusion-tube pressing parts are sequentially moved along the infusion tube such that a solution is delivered, the control unit performs control such that the rotating velocity of the motor becomes higher in accordance with an increase in the operating time of the motor.

Advantageous Effects of Invention

With the above configurations, as the infusion pump is provided with the restoration mechanism that presses two sides of the infusion tube pressed by the infusion-tube pressing part, the form of the infusion tube pressed and crushed by the infusion-tube pressing part may be restored even when it is a vinyl chloride infusion tube having low restorability, and a solution may be delivered in a stable manner even with the vinyl chloride infusion tube.

DESCRIPTION OF EMBODIMENTS

Figure 1:
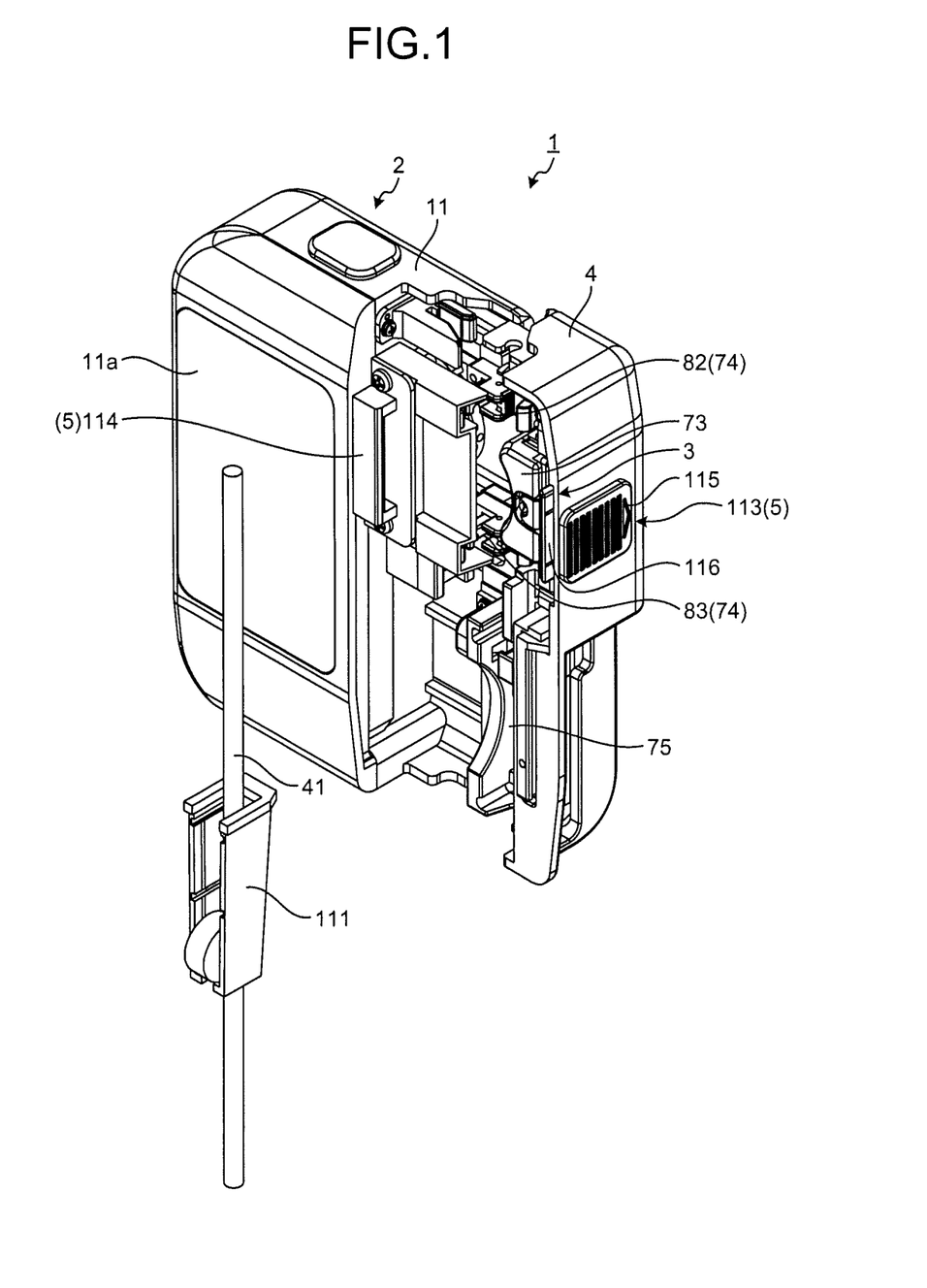
FIG. 1 is a perspective view that illustrates a state where a cover part of an infusion pump according to an embodiment of the present invention is opened.
Figure 2:
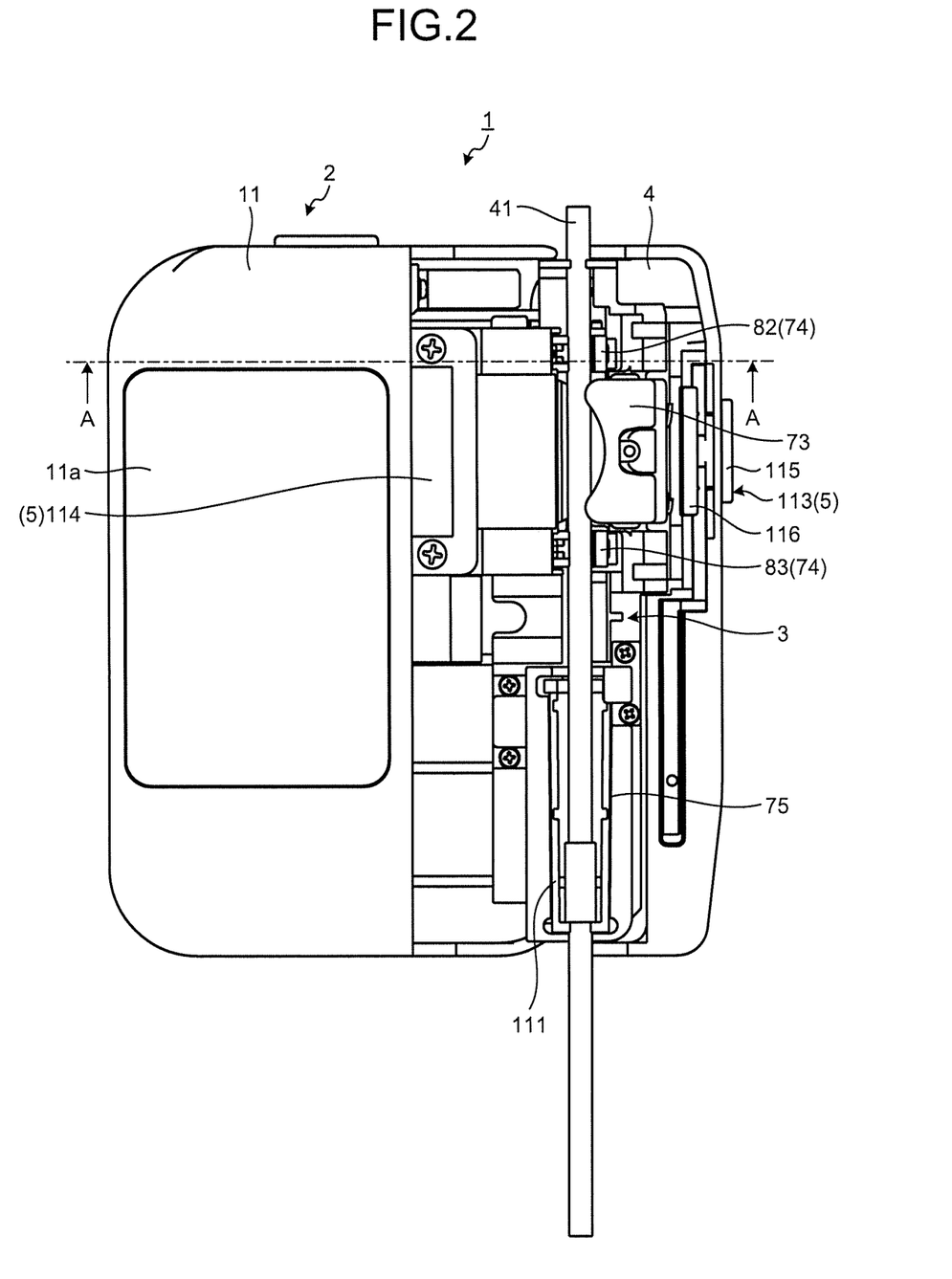
FIG. 2 is a front view of the infusion pump illustrated in FIG. 1.
Figure 3:
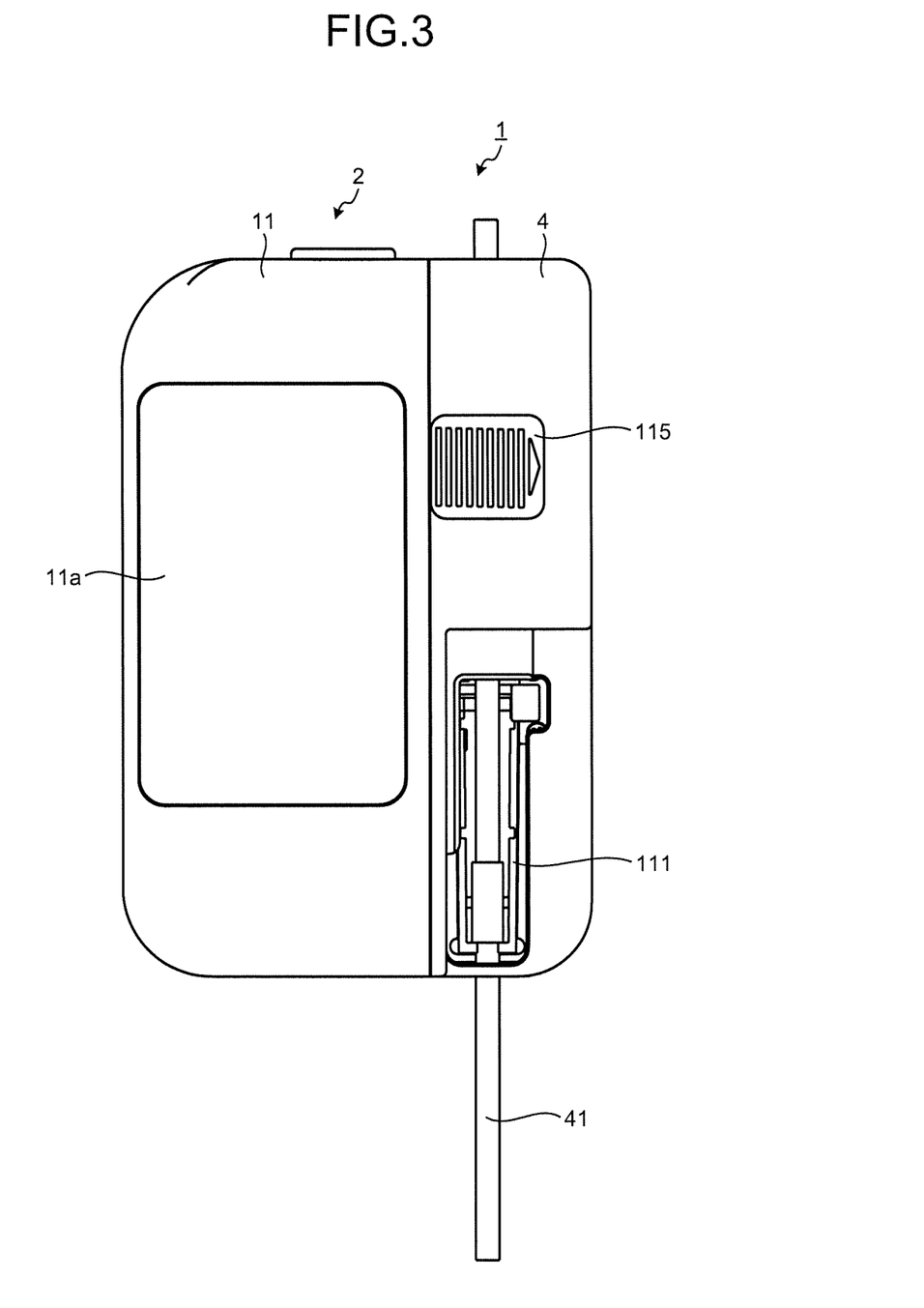
FIG. 3 is a front view that illustrates a state where the cover part of the infusion pump illustrated in FIG. 1 is closed.

A preferred embodiment of an infusion pump according to the present invention is described below in detail with reference to the accompanying drawings. FIG. 1 is a perspective view that illustrates the infusion pump. FIG. 2 is a front view that illustrates the infusion pump. An infusion pump 1 is a portable infusion pump and, as illustrated in FIG. 1 to FIG. 5, it includes an infusion-pump main body 2, a retraction part 3, a cover part 4, and an engagement mechanism 5. The infusion-pump main body 2 includes a chassis 11, a rotor unit 12, a motor 13, and a control unit 14. The chassis 11 is formed in a cuboidal box shape. The front surface of the chassis 11 is provided with a panel that is a touch panel as an operating unit 11a. The panel is operated so as to drive the motor 13 or adjust the speed of the solution delivered or the amount of solution delivered.

Figure 6:
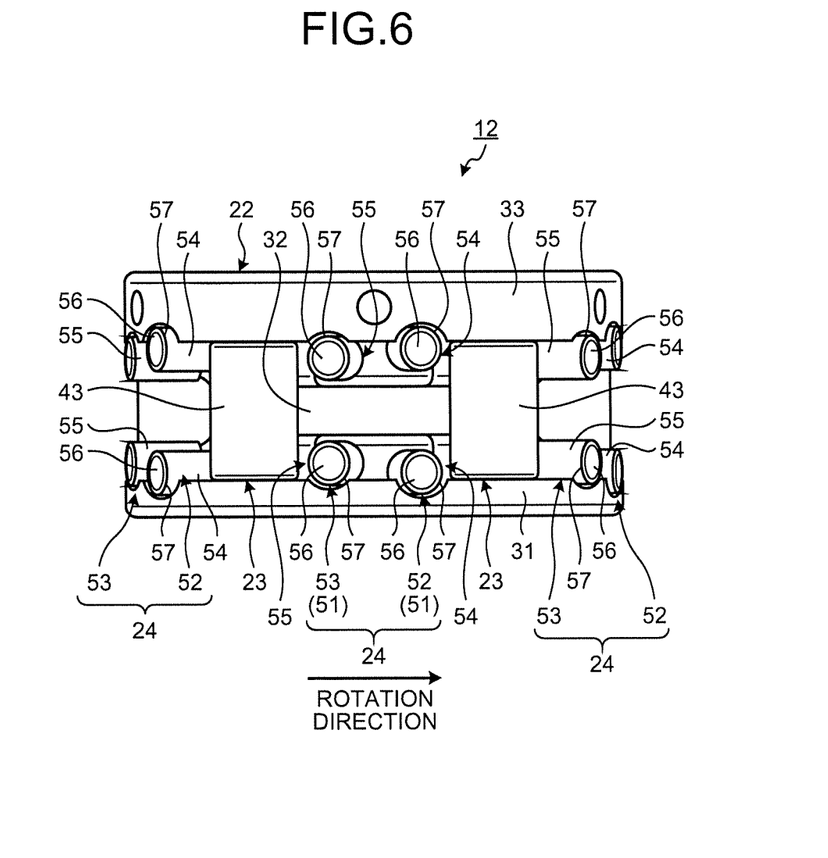
FIG. 6 is a side view that illustrates the rotor unit in the infusion pump illustrated in FIG. 1.
Figure 7:
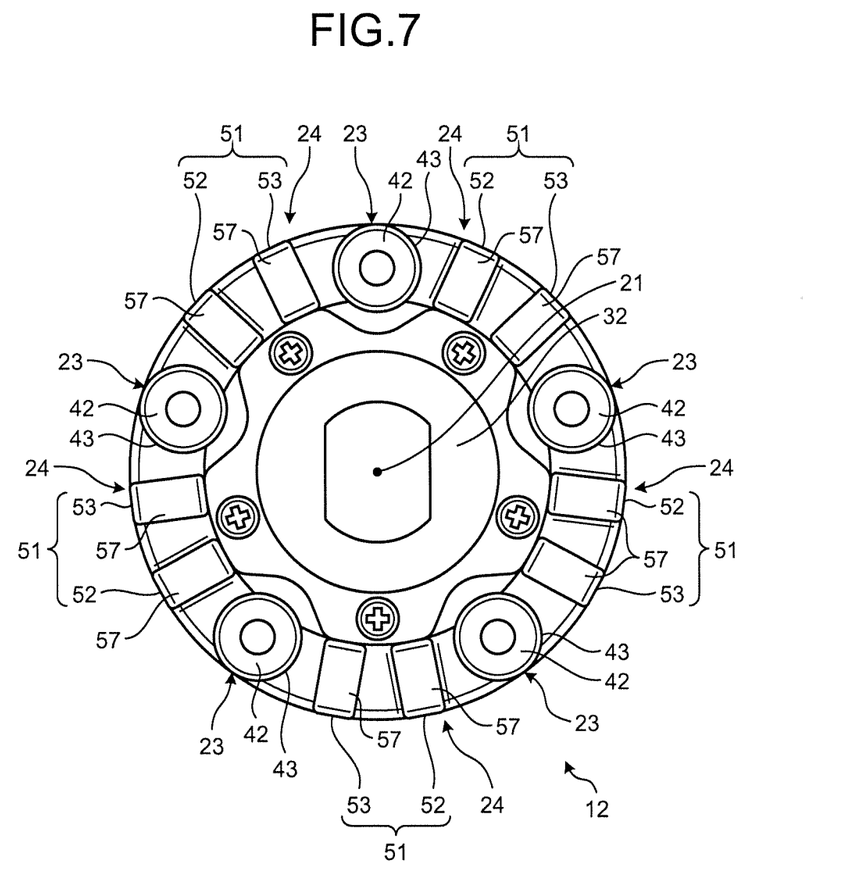
FIG. 7 is a front view that illustrates a state where a top plate of the rotor unit in the infusion pump illustrated in FIG. 1 is removed.

The rotor unit 12 is disposed such that it is rotatable around a rotary shaft 21 relative to the chassis 11 and, as illustrated in FIG. 6 and FIG. 7, it includes a rotor main body 22, a plurality of infusion-tube pressing parts 23, and a plurality of restoration mechanisms 24. The rotor main body 22 includes a circular bottom plate 31, a cylindrical part 32 that is mounted concentrically with the bottom plate 31 and has a diameter shorter than that of the bottom plate 31, and a top plate 33 that is mounted concentrically with the bottom plate 31, has the same diameter as that of the bottom plate 31, and is opposed to the bottom plate 31 through the cylindrical part 32. The central axis of the cylindrical part 32 is the rotary shaft 21 of the rotor main body 22.

The infusion-tube pressing parts 23 press a flexible infusion tube 41 and are disposed at equal intervals on the circumference with the rotary shaft 21 as a center. The infusion-tube pressing part 23 is a cylindrical roller that is configured such that a cylindrical part 43 rotates around a cylindrical rotary shaft 42, and it is parallel to the rotary shaft 21. The infusion-tube pressing part 23 is provided such that the outer circumference thereof coincides with the outer circumferences of the top plate 33 and the bottom plate 31 of the rotor main body 22. The interval between the infusion-tube pressing parts 23 is set to obtain a state where, when the rotor unit 12 is rotated, one of the infusion-tube pressing parts 23 always presses the infusion tube 41 in the space with an infusion-tube receiving member 73 described later. The length of the cylindrical part 43 of the infusion-tube pressing part 23 in its extending direction is formed to be larger than the outer diameter of the infusion tube 41 when it is crushed.

The restoration mechanism 24 is provided between the infusion-tube pressing parts 23, and it moves along an infusion-tube receiving surface 81 described later together with the infusion-tube pressing part 23 so as to press two sides of the infusion tube 41 pressed by the infusion-tube pressing part 23. The restoration mechanism 24 includes an infusion-tube insertion part 51 through which the infusion tube 41 passes. The infusion-tube insertion part 51 includes a first insertion part 52 and a second insertion part 53 having a small space for passing the infusion tube 41 as compared with the first insertion part 52. The first insertion part 52 and the second insertion part 53 are disposed such that, after the infusion-tube pressing part 23 passes the infusion tube 41, the first insertion part 52 passes and then the second insertion part 53 passes.

The first insertion part 52 and the second insertion part 53 are formed of a pair of cylindrical rollers disposed on the same circumference as that of the infusion-tube pressing part 23. First rollers 54, which are rollers of the first insertion part 52, are disposed such that the pitch between the first rollers 54 is equivalent to the outer diameter of the infusion tube 41 at normal times. Second rollers 55, which are rollers of the second insertion part 53, are disposed such that the pitch between the second rollers 55 is narrower than the outer diameter of the infusion tube 41 at normal times. The first and the second rollers 54, 55 are configured such that a cylindrical part 57 rotates around a cylindrical rotary shaft 56. The first and the second rollers 54, 55 are disposed such that the rotary shaft 56 is substantially perpendicular to the rotary shaft 21 of the rotor unit 12 and extends in the radial direction of the top plate 33. The first and the second rollers 54, 55 are rollers having a diameter shorter than that of the infusion-tube pressing part 23. The first and the second rollers 54, 55 are formed to have the identical diameter.

The motor 13 rotates the rotor unit 12, and a rotary shaft 61 rotates with a battery as a driving source. The motor 13 is disposed such that the rotary shaft 61 is parallel to the rotary shaft 21 of the rotor unit 12. Furthermore, a planetary-gear reduction mechanism 62 is provided between the motor 13 and the rotor unit 12. Although not illustrated, the planetary-gear reduction mechanism 62 includes a sun gear and a planetary gear, and it is disposed such that a rotary shaft 63 of the sun gear is parallel to the rotary shafts 21 and 61 of the rotor unit 12 and the motor 13.

The control unit 14 controls the rotating velocity of the motor 13 and, when the rotor unit 12 is rotated and the infusion-tube pressing parts 23 are sequentially moved along the infusion tube 41 so that the solution is delivered, controls the rotating velocity of the motor 13 such that the rotating velocity of the motor 13 becomes higher in accordance with an increase in the operating time of the motor 13. Furthermore, in a case where the control unit 14 controls the flow rate of liquid flowing through the infusion tube 41, the relationship between the time and the flow rate due to the infusion tube 41 used for infusion using the infusion pump 1 may be previously collected from experiments and generated as a function so that a control is performed based on the function.

The retraction part 3 has a pair of screws 71 provided in the chassis 11 inserted thereinto and is slidably movable in a direction close to the rotor unit 12 and in a direction away from it. The retraction part 3 is biased by a spring 71a in the direction of the arrow in FIG. 4, i.e., in the direction away from the rotor unit 12. The inner side of the retraction part 3 is provided with a cover abutting part 72 that abuts the cover part 4. The retraction part 3 includes the infusion-tube receiving member 73, a pair of infusion-tube holding parts 74, and a klemme mounting part 75.

The infusion-tube receiving member 73 includes the infusion-tube receiving surface 81 that serves as a receiving surface when the infusion-tube pressing part 23 presses the infusion tube 41. While the infusion tube 41 is sandwiched and pressed between the infusion-tube receiving surface 81 and the infusion-tube pressing part 23, the infusion-tube pressing parts 23 are sequentially moved in the longitudinal direction of the infusion tube 41 along the infusion-tube receiving surface 81 so that the liquid in the infusion tube 41 is delivered in one direction.

The infusion-tube receiving surface 81 is formed to be recessed and is disposed to be opposed to the rotor unit 12. The infusion-tube receiving surface 81 is formed to be circular around the rotary shaft 21 of the rotor unit 12 when the retraction part 3 is located closet to the rotor unit 12, i.e., when the infusion tube 41 is pressed by the infusion-tube pressing part 23 and the infusion-tube receiving surface 81. The retraction part 3 approaches the rotor unit 12 until the infusion tube 41 is closed when the infusion tube 41 is pressed by the infusion-tube pressing part 23 and the infusion-tube receiving surface 81.

Figure 9:
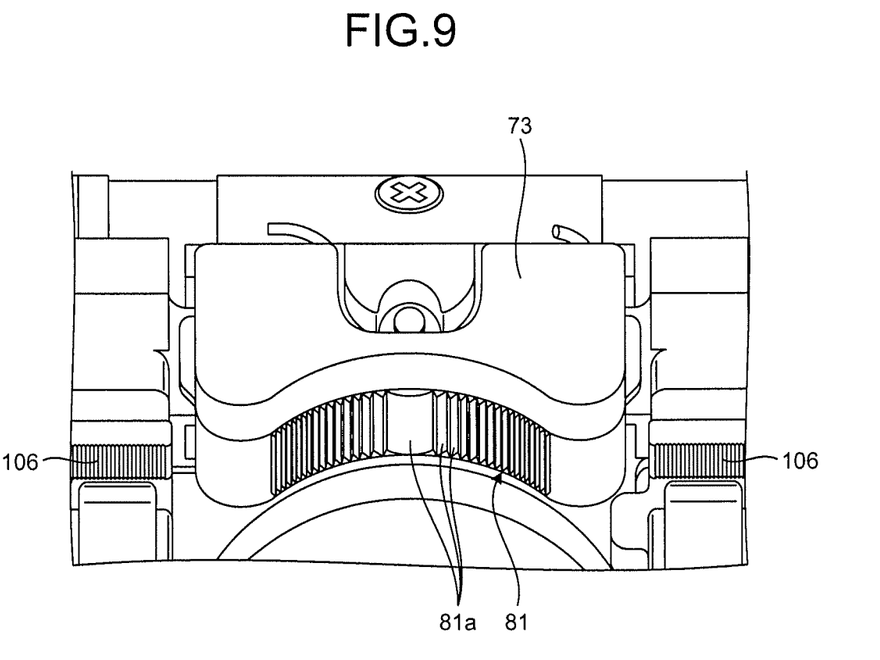
FIG. 9 is a perspective view that illustrates an infusion-tube receiving member in the infusion pump illustrated in FIG. 1.

The infusion-tube receiving surface 81 is formed such that the rotor unit 12 is engaged with the infusion-tube receiving surface 81 through the infusion tube 41. The infusion-tube receiving surface 81 has the width dimension nearly equal to that of the infusion-tube pressing part 23. As illustrated in FIG. 9, the infusion-tube receiving surface 81 includes recesses and protrusions 81a that prevent a relative movement of the infusion tube 41.

Figure 8:
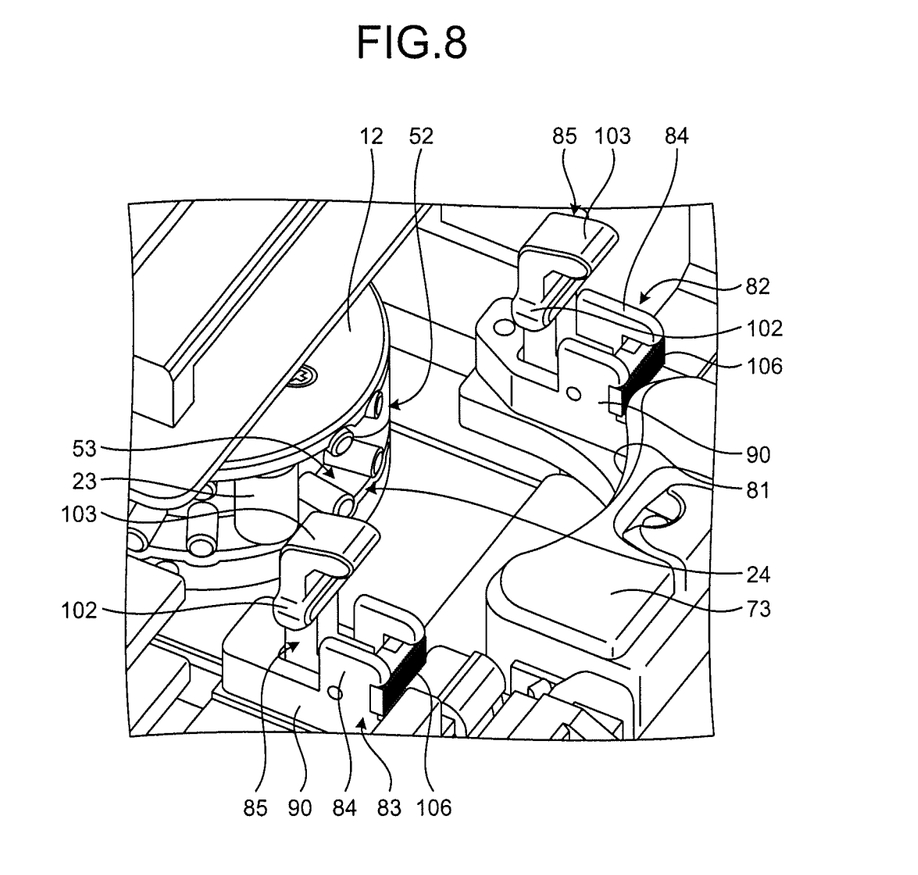
FIG. 8 is a perspective view that illustrates the relevant part of the infusion pump illustrated in FIG. 1.

The pair of infusion-tube holding parts 74 holds the infusion tube 41 to prevent the movement of the infusion tube 41 in its longitudinal direction. The infusion-tube holding parts 74 in pair are disposed on two sides of the infusion-tube receiving surface 81 in the longitudinal direction of the infusion-tube receiving surface 81, as illustrated in FIG. 8. Specifically, the infusion-tube holding parts 74 are located on the upstream side and the downstream side with the infusion-tube receiving member 73 interposed therebetween. The infusion-tube receiving surface 81 and the infusion-tube pressing part 23 are movable to have a wider space between each other, and the infusion-tube holding parts 74 in pair are disposed so as to move in a direction away from each other while holding the infusion tube 41 before the infusion-tube pressing part 23 and the infusion-tube receiving surface 81 press the infusion tube 41 after the infusion-tube pressing part 23 and the infusion-tube receiving surface 81 have a wide space between each other.

Figure 5:
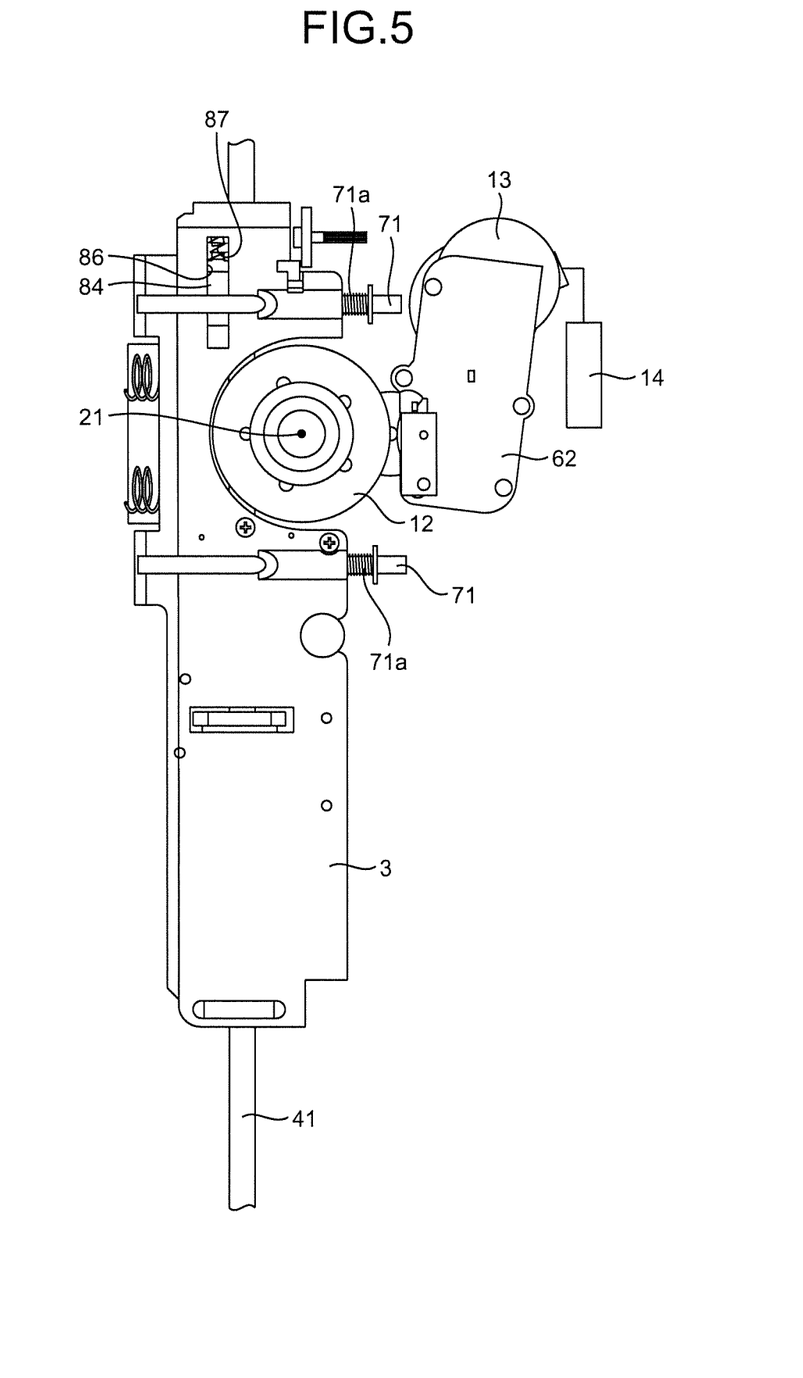
FIG. 5 is a back view that illustrates the retraction part and the rotor unit in the infusion pump illustrated in FIG. 1.

The pair of infusion-tube holding parts 74 includes: a first holding part 82 that holds the upstream side of the infusion tube 41; and a second holding part 83 that holds the downstream side of the infusion tube 41. The first holding part 82 and the second holding part 83 include a base part 84 and a rotary member 85. As illustrated in FIG. 5, the base part 84 of the first holding part 82 is engaged with a movement groove 86 formed on the retraction part 3 and extending in the longitudinal direction of the infusion-tube receiving member 73, and it is disposed so as to move in the extending direction of the infusion tube 41. The base part 84 of the first holding part 82 is biased by a spring 87 in a direction close to the second holding part 83. The first holding part 82 may be moved so as to increase the interval between the first holding part 82 and the second holding part 83 by approximately 10%. The base parts 84 of the first holding part 82 and the second holding part 83 include: a rotary-member support part 90 that pivotally supports the rotary member 85; a bottom part 91 including a bottom surface 91a that abuts the infusion tube 41; a first side part 92 including a first side surface 92a that abuts the infusion tube 41; and a second side part 93 including a second side surface 93a that abuts the infusion tube 41.

Figure 10:
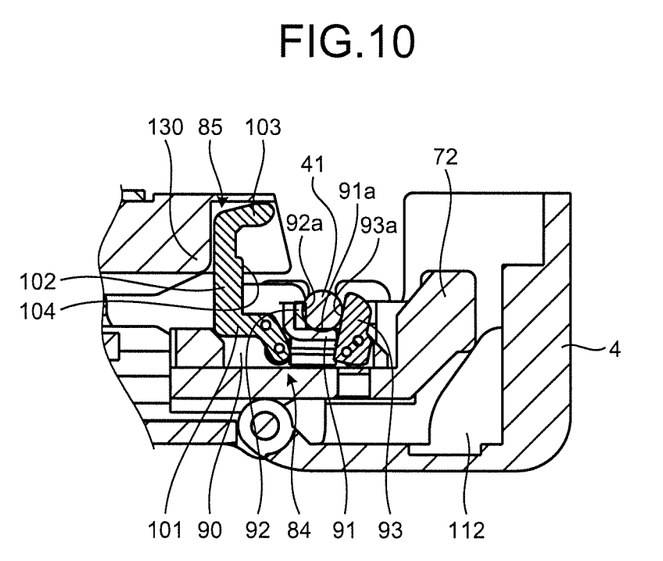
FIG. 10 is a partial cross-sectional view in the A-A illustrated in FIG. 2.
Figure 11:
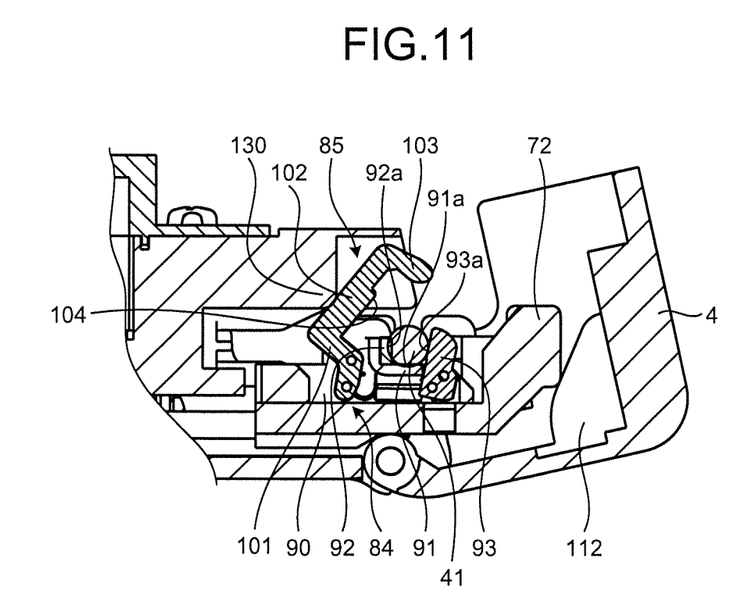
FIG. 11 is a partial cross-sectional view in the process of closing the cover part of the infusion pump illustrated in FIG. 10.

As illustrated in FIG. 10 and FIG. 11, the rotary members 85 of the first holding part 82 and the second holding part 83 include: a first main body part 101 that has a cuboidal shape; a second main body part 102 that has a cuboidal shape and protrudes from one end of the first main body part 101 in a direction perpendicular to the first main body part 101; and an end part 103 that protrudes from one end of the second main body part 102 in the same direction as the first main body part 101. The first main body part 101 is rotatably and pivotally supported by the chassis 11, and the rotary member 85 is rotatable in the direction (closing direction) to hold the infusion tube 41 and in the direction (opening direction) to release the infusion tube 41. Furthermore, the first main body part 101 is biased in the opening direction.

The second main body part 102 is provided with a top surface 104 that abuts the infusion tube 41. When the rotary member 85 is rotated in the closing direction, the end part 103 abuts the surface of the second side part 93 at the opposite side of the second side surface 93a abutting the infusion tube 41 and presses the second side part 93 in the direction to abut the infusion tube 41.

The bottom part 91, the first side part 92, the second side part 93, and the second main body part 102 constitute a tube through-hole 105 having a rectangular shape in cross-section. The bottom surface 91a, the first side surface 92a, the second side surface 93a, and the top surface 104 are areas abutting the infusion tube 41, and the first side surface 92a and the second side surface 93a are provided with recesses and protrusions 106 to prevent a relative movement of the infusion tube 41.

The klemme mounting part 75 is a part to which a klemme 111 is attached. The klemme mounting part 75 is a recessed part that is formed in the retraction part 3 on the downstream side of the infusion-tube receiving member 73, and it is engaged with the klemme 111.

The cover part 4 includes a window part having an opening on its front surface, and it rotates around a rotary shaft provided in the infusion-pump main body 2 to be opened and closed relative to the infusion-pump main body 2. In FIG. 1, the cover part 4 is formed to cover the right side part of the chassis 11. The inner side of the cover part 4 is provided with an abutting part 112 that abuts the cover abutting part 72 of the retraction part 3 to move the retraction part 3. The abutting part 112 is formed to protrude toward the inner side of the cover part 4.

The engagement mechanism 5 engages the cover part 4 with the infusion-pump main body 2, and it slides and moves from the engaged state to cancel the engagement. The engagement mechanism 5 includes a slide part 113 provided in the cover part 4 and an engaged part 114 provided in the infusion-pump main body 2. The slide part 113 includes an operating part 115 operated by the operator and an engaging part 116 engaged with the engaged part 114. When the cover part 4 is closed, the engaging part 116 is engaged with the engaged part 114 in the engagement mechanism 5 so that the cover part 4 is prevented from being opened. When the operating part 115 is slid and moved, the engaged state between the engaging part 116 and the engaged part 114 in the engagement mechanism 5 is canceled so that the cover part 4 may be opened.

Figure 12:
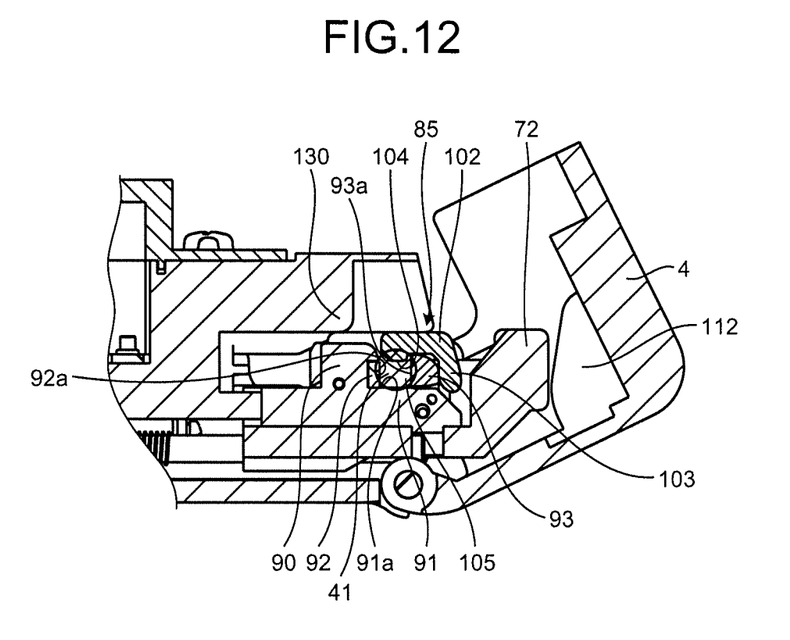
FIG. 12 is a partial cross-sectional view that illustrates a state where the cover part is further moved in a closing direction in the infusion pump illustrated in FIG. 11.

As illustrated in FIG. 2 and FIG. 10, in the portable infusion pump 1 having the above configuration, the infusion tube 41 is attached to the infusion-tube holding parts 74 in a state where the cover part 4 is opened. In this state, the rotary member 85 of the infusion-tube holding part 74 is in an upright state. Furthermore, as illustrated in FIG. 11, when the cover part 4 is moved in the closing direction, the abutting part 112 of the cover part 4 abuts the cover abutting part 72 of the retraction part 3 so that the retraction part 3 starts to move toward the rotor unit 12. At this point, the rotary member 85 of the infusion-tube holding part 74 abuts a ceiling part 130 of the chassis 11 and starts to rotate in a direction to hold the infusion tube 41. Furthermore, when the cover part 4 is further rotated in the closing direction, the retraction part 3 is further moved toward the rotor unit 12 and the rotary member 85 is also further rotated so that the infusion-tube holding parts 74 hold the infusion tube 41, as illustrated in FIG. 12. At this point, the end part 103 of the infusion-tube holding part 74 abuts the surface of the second side part 93 on the opposite side of the second side surface 93*a*, which is the surface abutting the infusion tube 41, to press the second side part 93 in the direction to abut the infusion tube 41. Therefore, in this state, the infusion tube 41 is held by the first side surface 92*a* and the second side surface 93*a*. Furthermore, at this point, the second main body part 102 of the infusion-tube holding part 74 is pressed by the ceiling part 130 of the chassis 11 so that the top surface 104 of the second main body part 102 is pressed against the infusion tube 41. Thus, the infusion tube 41 is held by the top surface 104 and the bottom surface 91*a*.

Figure 13:
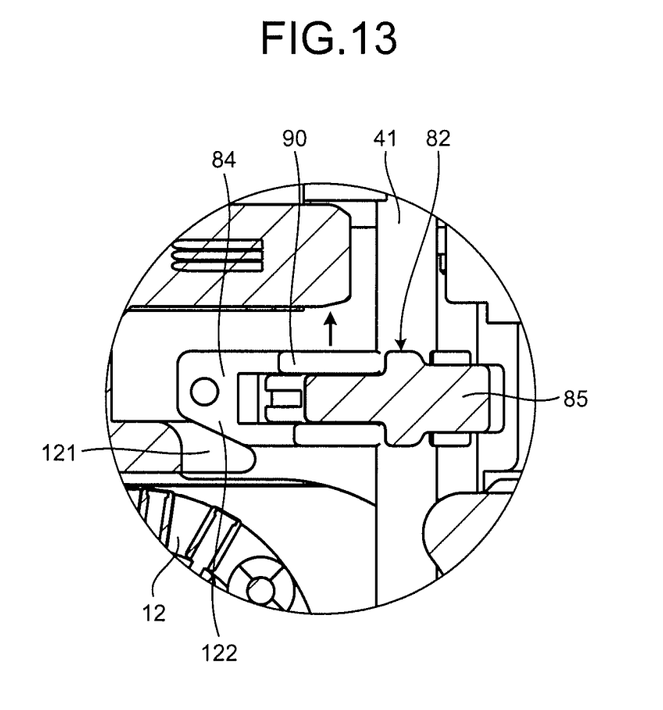
FIG. 13 is a front-side partial cross-sectional view that illustrates a first holding part of the infusion pump illustrated in FIG. 1.

Furthermore, after the cover part 4 is closed and it is ensured that the infusion tube 41 is held by the infusion-tube holding parts 74, a cam abutting part 122 of the first holding part 82 of the infusion-tube holding part 74 abuts a cam part 121 provided in the chassis 11 and is pressed by the cam part 121 so that the first holding part 82 moves in the direction (the direction of the arrow in the figure) to stretch the infusion tube 41, as illustrated in FIG. 13. As a result, the infusion tube 41 is stretched.

Figure 4:
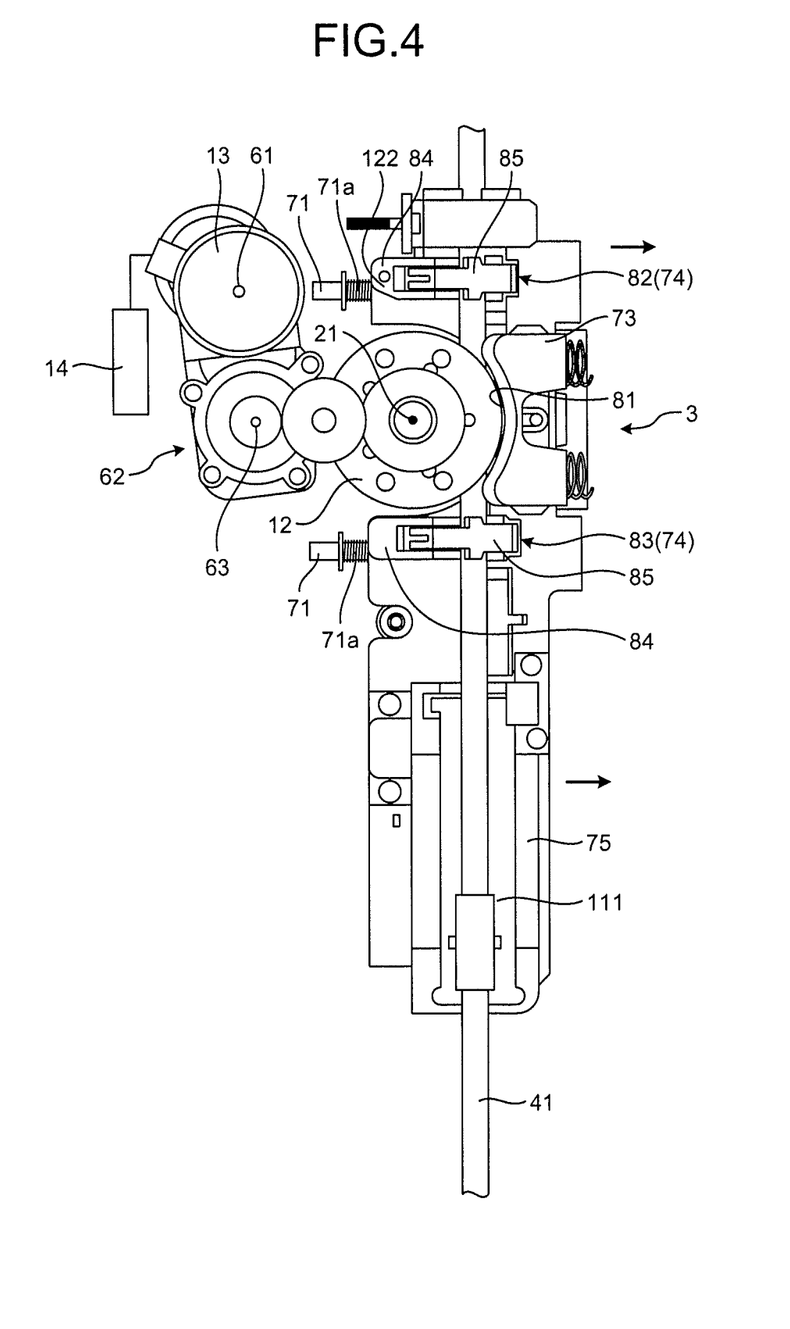
FIG. 4 is a front view that illustrates a retraction part and a rotor unit in the infusion pump illustrated in FIG. 1.

After the cover part 4 is completely closed, the retraction part 3 is moved until the rotor unit 12 abuts the infusion-tube receiving member 73 with the infusion tube 41 interposed therebetween, the infusion tube 41 is pressed by the infusion-tube pressing part 23 and the infusion-tube receiving surface 81, and the infusion tube 41 is closed, as illustrated in FIG. 4. In this state, when a roller of the klemme 111 is moved in the direction to release the infusion tube 41, a solution deliverable state is obtained. Then, by operating the operating unit 11*a* to drive the motor 13, the solution is delivered.

The above-described portable infusion pump 1 includes the restoration mechanism 24 that presses two sides of the infusion tube 41 pressed by the infusion-tube pressing part 23; thus, the form of the infusion tube 41 pressed and deformed by the infusion-tube pressing part 23 may be restored by the restoration mechanism 24 in a desirable manner. Thus, it is possible to deliver the solution in a stable manner even when the vinyl chloride infusion tube 41, which has a low restoring force as compared with a silicon tube, is used in the infusion pump 1.

Furthermore, the restoration mechanism 24 includes the infusion-tube insertion part 51 having a space for passing the infusion tube 41, the infusion-tube insertion part 51 includes the first insertion part 52 and the second insertion part 53 having a small space for passing the infusion tube 41 as compared with the first insertion part 52, and the first insertion part 52 and the second insertion part 53 are disposed such that, after the infusion-tube pressing part 23 passes the infusion tube 41, the first insertion part 52 passes and then the second insertion part 53 passes; thus, the infusion tube 41 pressed and deformed by the infusion-tube pressing part 23 is pressed at two sides thereof by the first insertion part to be restored to a certain degree and is further pressed at two sides thereof by the second insertion part to be further restored. Thus, the deformed infusion tube 41 may be restored to have the original form in a desirable manner so that the solution may be delivered in a stable manner.

When the infusion pump 1 conducts infusion, the infusion-tube pressing part 23 moves while pressing the infusion tube 41, and therefore the infusion tube 41 is stretched. The largely stretched infusion tube 41 interrupts the stable solution delivery. According to the above-described embodiment, however, when the cover part 4 is closed, the first holding part 82 moves in a direction away from the second holding part 83 to stretch the infusion tube 41 in advance while the infusion-tube holding parts 74 hold the infusion tube 41, whereby the infusion tube 41 is less stretched in use so that the solution may be delivered in a stable manner.

The part of the infusion-tube receiving surface 81 abutting the infusion tube 41 is provided with the recesses and protrusions 81*a* to prevent a relative movement of the infusion tube 41; thus, the movement of the infusion tube 41 may be prevented in a desirable manner, and the solution may be delivered in a stable manner.

The planetary-gear reduction mechanism 62 provided between the motor 13 and the rotor unit 12 allows the rotary shafts 61 and 21 of the motor 13 and the rotor unit 12 to be parallel to each other and achieves a reduction in the size of the infusion pump 1.

During the solution delivery, the control unit 14 performs control such that the rotating velocity of the motor 13 becomes higher in accordance with an increase in the operating time of the motor 13; thus, it is possible to prevent the amount of solution delivered by the infusion pump 1 from decreasing beyond a certain level with time.

Furthermore, the infusion-tube pressing part 23 does not need to be a roller and may be formed to protrude from the cylindrical part 32. Although the infusion tube 41 is held by the infusion-tube holding part 74 on four surfaces thereof, it may be held on two surfaces or may be held on three surfaces. The recesses and protrusions 106 preventing a relative movement may be formed on at least one surface among the surfaces abutting the infusion tube 41. The recesses and protrusions 106 preventing a relative movement may be formed on two surfaces or formed on more than two surfaces among the surfaces abutting the infusion tube 41.

REFERENCE SIGNS LIST

1 INFUSION PUMP
2 INFUSION-PUMP MAIN BODY
3 RETRACTION PART
4 COVER PART
5 ENGAGEMENT MECHANISM
11 CHASSIS
11a OPERATING UNIT
12 ROTOR UNIT
13 MOTOR
14 CONTROL UNIT
22 ROTOR MAIN BODY
23 INFUSION-TUBE PRESSING PART
24 RESTORATION MECHANISM
41 INFUSION TUBE
81 INFUSION-TUBE RECEIVING SURFACE

The invention claimed is:

1. An infusion pump comprising:
  infusion-tube pressing parts configured to press a flexible infusion tube;
  an infusion-tube receiving surface configured to serve as a receiving surface when the infusion-tube pressing parts press the infusion tube;
  a restoration device provided between the infusion-tube pressing parts, the restoration device being configured to move together with the infusion-tube pressing parts along the infusion-tube receiving surface and to press two sides of the infusion tube pressed by the infusion-tube pressing parts; and
  a pair of infusion-tube holding parts configured to hold the infusion tube in a longitudinal direction of the infusion-tube receiving surface at areas on two sides with the infusion-tube receiving surface interposed therebetween,
  wherein the infusion-tube pressing parts are configured to move sequentially in a longitudinal direction of the infusion tube along the infusion-tube receiving surface to deliver a liquid in the infusion tube in one direction while pressing the infusion tube by sandwiching the infusion tube with the infusion-tube receiving surface,
  wherein the restoration device includes an infusion-tube insertion part having a space for passing the infusion tube,
  wherein the infusion-tube insertion part includes:
    a first insertion part; and
    a second insertion part having a smaller space for passing the infusion tube as compared with the first insertion part,
  wherein the first insertion part and the second insertion part are disposed such that the second insertion part passes the infusion tube after the first insertion part passes the infusion tube,
  wherein the first insertion part is formed of a first pair of rollers, and the second insertion part is formed of a second pair of rollers,
  wherein the infusion-tube pressing parts and the infusion-tube receiving surface are movable to have a wider space between each other, and
  wherein when the infusion-tube pressing parts and the infusion-tube receiving surface moves from a state of having a wide space between each other to a state where the infusion tube is pressed by the infusion-tube pressing parts and the infusion-tube receiving surface, the pair of infusion-tube holding parts are moved in a direction away from each other, while holding the infusion tube, before the infusion tube is pressed by the infusion-tube pressing parts and the infusion-tube receiving surface, and
  wherein the pair of infusion-tube holding parts include:
    a first holding part including a first base part and a first rotary member; and
    a second holding part including a second base part and a second rotary member.

2. The infusion pump according to claim 1, wherein a part of the infusion-tube receiving surface abutting the infusion tube is provided with a recess and a protrusion to prevent a relative movement of the infusion tube.

3. The infusion pump according to claim 1, further comprising:
  a rotor that is disposed to be rotatable around a rotary shaft, the rotor being configured to support the infusion-tube pressing parts on a circumference around the rotary shaft and to support the restoration device between the infusion-tube pressing parts; and
  an infusion-tube receiving member that is formed such that, when the infusion tube is pressed by the infusion-tube pressing parts and the infusion-tube receiving surface, the infusion-tube receiving surface has a circular shape with the rotary shaft of the rotor as a center.

4. The infusion pump according to claim 3, further comprising:
  a motor configured to rotate the rotor; and
  a planetary-gear reduction device provided between the motor and the rotor such that a rotary shaft of a sun gear is parallel to the rotary shaft of the rotor.

5. The infusion pump according to claim 3, further comprising:
  a motor configured to rotate the rotor; and
  a controller configured to control a rotating velocity of the motor, wherein
  when the rotor is rotated and the infusion-tube pressing parts are sequentially moved along the infusion tube such that a liquid is delivered, the controller performs control such that the rotating velocity of the motor becomes higher in accordance with an increase in an operating time of the motor.

6. The infusion pump according to claim 1, wherein
  the first pair of rollers, which are the rollers of the first insertion part, are disposed such that a pitch between the first pair of rollers is equivalent to an outer diameter of the infusion tube at normal times, and
  the second pair of rollers, which are the rollers of the second insertion part, are disposed such that the pitch between the second pair of rollers is narrower than the outer diameter of the infusion tube at normal times.

7. The infusion pump according to claim 1, wherein the first base part is configured to:
  engage with a groove
    formed on a retraction part, and
    extending in a longitudinal direction of an infusion-tube receiving member; and
  move in an extending direction of the infusion tube.

* * * * *

UNITED STATES PATENT AND TRADEMARK OFFICE
CERTIFICATE OF CORRECTION

| | |
|---|---|
| PATENT NO. | : 11,331,426 B2 |
| APPLICATION NO. | : 16/496358 |
| DATED | : May 17, 2022 |
| INVENTOR(S) | : Katsuya Kono et al. |

It is certified that error appears in the above-identified patent and that said Letters Patent is hereby corrected as shown below:

On the Title Page

Under Assignee:
"NITRO CORPORATION, Osaka (JP)" should read --NIPRO CORPORATION, Osaka, (JP)--

Signed and Sealed this
Eighteenth Day of October, 2022

Katherine Kelly Vidal
*Director of the United States Patent and Trademark Office*